United States Patent
Morsdorf et al.

[11] Patent Number: 6,132,256
[45] Date of Patent: *Oct. 17, 2000

[54] DESIGN OF A LAMBDA MODULE WITH MATING PLUG

[75] Inventors: Tabitha Morsdorf, Stetten; Dirk Schimansky, Bonn, both of Germany

[73] Assignee: Augat Components GmbH, division of Thomas & Betts, Egelsbach, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 09/068,310
[22] PCT Filed: Sep. 11, 1997
[86] PCT No.: PCT/DE97/02047
   § 371 Date: Sep. 10, 1998
   § 102(e) Date: Sep. 10, 1998
[87] PCT Pub. No.: WO98/11632
   PCT Pub. Date: Mar. 19, 1998

[30] Foreign Application Priority Data

Sep. 11, 1996 [DE] Germany .......................... 296 15 862

[51] Int. Cl.[7] .................................................. H01R 13/66
[52] U.S. Cl. ............................................................ 439/620
[58] Field of Search ...................................... 439/76.1, 595, 439/752, 587, 588, 589, 620

[56] References Cited

U.S. PATENT DOCUMENTS

| | | | |
|---|---|---|---|
| 4,412,714 | 11/1983 | Morningstar et al. | 439/466 |
| 5,490,785 | 2/1996 | Hein et al. | 439/76.1 |
| 5,529,515 | 6/1996 | Ohtaka et al. | 439/595 |
| 5,820,409 | 10/1998 | Clark et al. | 439/595 |

FOREIGN PATENT DOCUMENTS

| | | |
|---|---|---|
| 0 120 423 A1 | 10/1984 | European Pat. Off. . |
| 0 613 216 A1 | 8/1994 | European Pat. Off. . |
| 42 35 181 A1 | 7/1993 | Germany . |

*Primary Examiner*—Tulsidas C. Patel
*Attorney, Agent, or Firm*—Oliff & Berridge, PLC

[57] ABSTRACT

A lambda module for motor vehicle catalytic converters includes a module housing having a mount supporting a hybrid module and inserted electrical contacts. A receptacle is provided in the module housing to receive a mating plug. The mount supporting the hybrid module is a frame that engages the hybrid module at its circumference. The frame holds the hybrid module so that the hybrid module is accessible from its top in an unassembled state. A cap is mounted on the frame in an assembled state surrounding the hybrid module in a sealing manner and locked to the remainder of the module housing.

14 Claims, 2 Drawing Sheets

DESIGN OF A LAMBDA MODULE WITH MATING PLUG

BACKGROUND OF THE INVENTION

1. Field of the Invention

The subject of the invention is a lambda module with a mating plug for lambda probes of catalytic converters.

2. Description of the Related Art

A lambda module of this type consists, as is known, of a housing in which an electronic hybrid module with the corresponding two electrical terminals is accommodated. A plug-in connector is molded on the housing, into which connector the mating plug, mounted on a connecting cable, can be inserted and locked.

SUMMARY OF THE INVENTION

The object of the invention is to provide a design for a lambda module of this type that is especially advantageous and easily assembled, especially with regard to the mounting of the hybrid module. In previous designs, soldering the contacts to the hybrid module and the required adjustment posed problems.

This objective is achieved according to the invention by the design described in the claims.

An embodiment of the invention will now be described in greater detail with reference to the attached drawings.

DESCRIPTION OF THE PREFERRED EMBODIMENT

Figure 1:
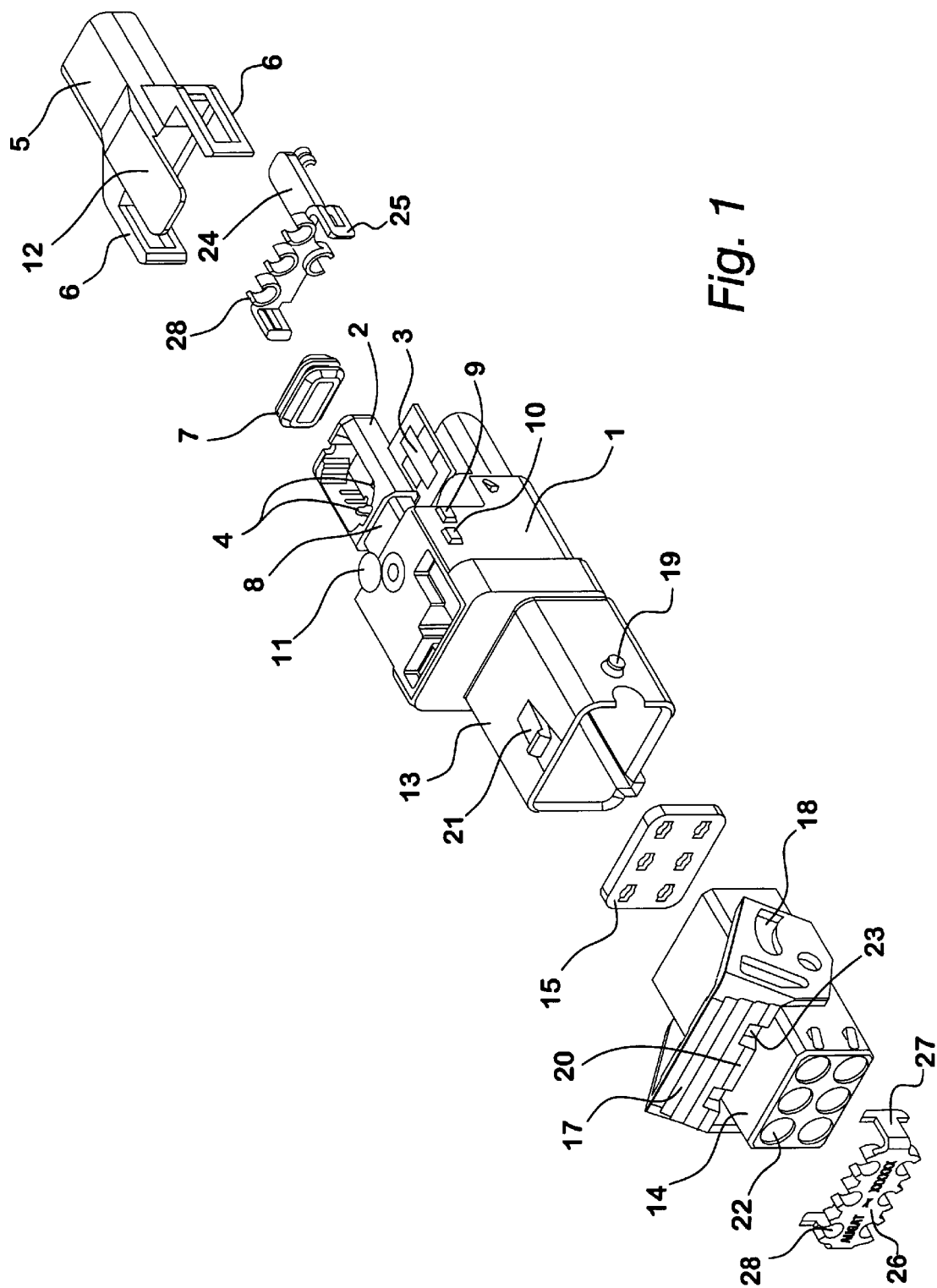
FIG. 1 shows the lambda module together with the mating plug in an exploded perspective view.

The lambda module consists of a module housing 1 with a molded module carrier 2 for a hybrid module 3. Hybrid module 3, in the form of a small plate which serves for laser adjustment, can be inserted into the module carrier 2 from below in the embodiment shown and can be latched by means of latching noses provided thereon. In the chambers surrounded by module carrier 2 there are two contacts 4 molded into modular housing 1, said contacts being soldered to hybrid module 2 after it has been inserted.

Module carrier 3 is made in the shape of an open frame and thus surrounds a space that is open at the top and bottom. This frame can be a rectangular frame as shown, but it could also have only a fork- or U-shape. In the latter case (not shown) the hybrid module plate could also be inserted sideways like a drawer, in matching guide grooves for example.

The frame shape of module carrier 2 that surrounds hybrid module 3 only at its circumference allows free access to hybrid module 3 for laser adjustment and for soldering the contacts.

In order to protect contacts 4 and hybrid module 3 from water, oil, dirt, and other contaminants, a cap 5 is provided, said cap being capable of being pushed over module 3 carrier 2 following adjustment of the hybrid module and following soldering of the contacts, and latching by lateral latching arms 6 with matching latching noses molded on module housing 1. An annular seal 7 is mounted previously on neck 8 between module carrier 2 and the remainder of module housing 1, thus sealing the front end of cap 5 when mounted.

For latching cap 5, a first pair of latching noses 9 is formed on module housing 1 for preliminary latching and a second pair of latching noses 10 is provided for final latching.

In order to guarantee pressure equalization in the hybrid module chamber that is hermetically sealed when the cap is in place, a recess is provided in module housing 1, with a pressure equalizing membrane 11 glued onto said recess. This pressure equalizing membrane 11, when cap 5 is mounted, is protected by a covering tongue 12 molded on it so that it projects at the top, and is thus protected against mechanical damage and contamination.

On the other side of module housing 1 (relative to module carrier 2), a receptacle 13 is provided. This receptacle serves to receive a mating plug 14 with interposition of a sealing cushion 15. Mechanical encoding on the receptacle and (not visible in FIG. 1) on mating plug 14 prevents the mating plug from being inserted with the incorrect orientation.

To secure and lock mating plug 14 in receptacle 13, a pivotable tightening clip 17 is provided on the mating plug. This clip, with slotted links 18 provided on both sides, fits over pins 19 provided on both sides of receptacle 13. When the tightening clip is pivoted, therefore, as a result of the cooperation of slotted link 18 with pin 19, mating plug 14 is pulled completely into receptacle 13. The end portions of slotted links 18 are shaped so that a stable latching position is obtained as the final position. At the same time, the middle rib of tightening clip 17 fits by its rear edge area 20 over a flexible latching nose 21 on receptacle 13.

The mating plug, as can be seen from FIG. 1, is designed with a honeycomb inside, in other words a tubular chamber 22 is associated with each hole, with the chambers being separated from one another by partitions. As a result of this honeycomb structure, in cooperation with sealing cushion 15, water tightness is achieved between module housing 1 and mating plug 14 from one chamber to the next.

Tightening clip 17 of the mating plug, in the rear edge area of its middle rib, has two molded elastic latches 23, which, when the tightening clip is pivoted backward as shown, can engage behind the latching noses that are molded on mating plug 14 and are concealed in FIG. 1 and therefore not visible. As a result, tightening clip 17 can be locked in its open position on mating plug 14, so that it does not move out of position even during shipment (in bulk) and simplifies handling during assembly.

To protect the cable contacts (introduced into module housing 1 below module carrier 2), following their assembly, a secondary locking element 24 is clipped onto module housing 1. For this purpose, secondary lock 24 has latching arms 25 on both sides, said arms cooperating with matching latching noses molded on module housing 1.

Similarly, to secure the connecting cable contacts in mating plug 14, a secondary locking element 26 is provided, which, following installation of the cable contacts in the mating plug, is clipped to these contacts at the back and has latching arms 27 on both sides for this purpose, said arms cooperating with matching latching noses on mating plug 14. The secondary locking elements are each formed, as can be seen, with elements 28 that surround the cables pincerwise and have a precentering action.

Figure 2:
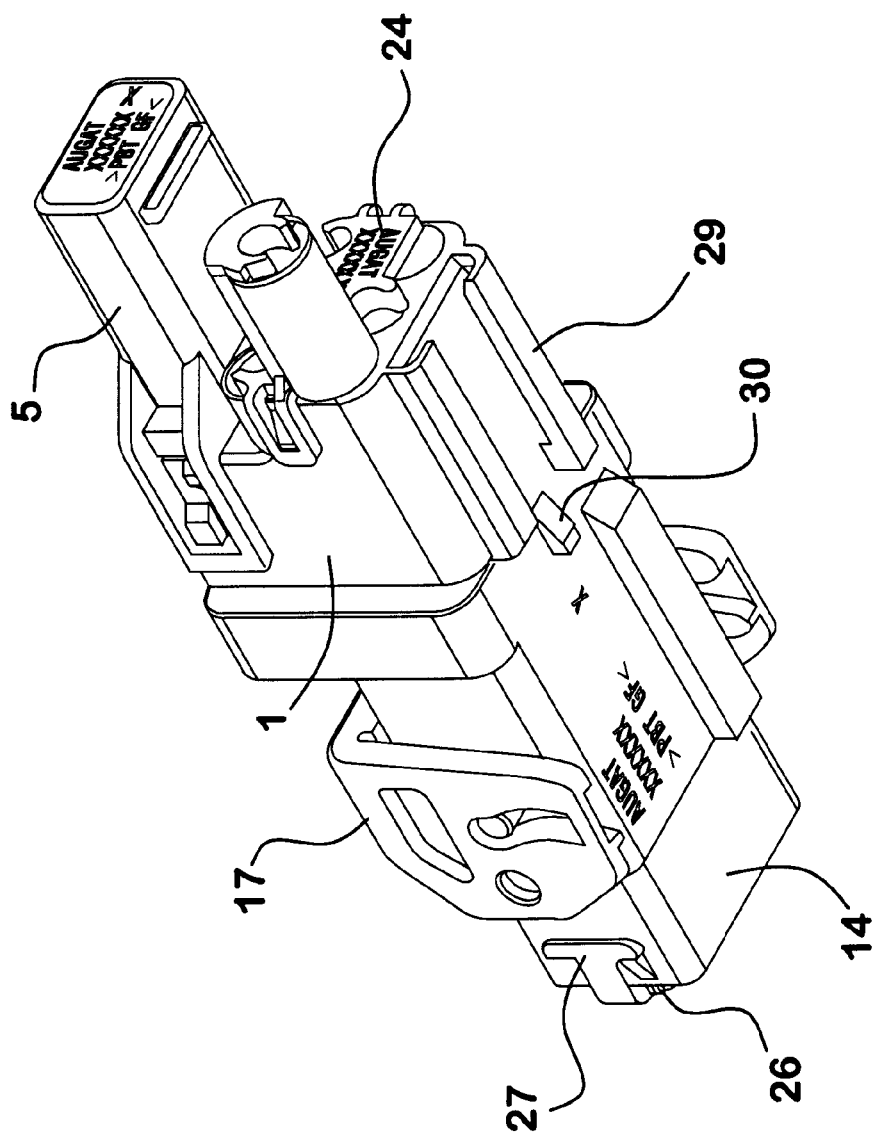
FIG. 2 shows the lambda module with the mating plug connected (but not showing the cable), likewise in a perspective view, but assembled and viewed from a different direction.

In FIG. 2, in which the lambda module is shown with cap 5 in place and mating plug 14 latched in position, a swallowtail receptacle 29 is located on the bottom of module housing 1 and a latching nose 30 for mounting the lambda module on a standard mounting device may be seen.

What is claimed is:

1. A lambda module for motor vehicle catalytic converters, comprising:

a module housing including a receptacle portion adapted to receive a mating plug;

a module carrier connected to said receptacle portion;

a cap mounted on said module carrier;

an electronic hybrid module in the form of a small plate mounted to said module carrier, said module carrier including a frame surrounding a space that is open at least at the top, and holding said hybrid module at the circumference thereof;

electrical contacts mounted in said receptacle portion and connected to said hybrid module, wherein said cap is adapted to sealingly surround said hybrid module and to be locked in position on said module carrier.

2. A lambda module according to claim 1, wherein said module carrier frame has one of a rectangular, a fork, and a U-shape and surrounds a space that is open both at the top and bottom.

3. A lambda module according to claim 1, wherein said module carrier has a neck-like projection connecting the module carrier to said receptacle portion of the module housing;

an annular seal is mounted on said neck-like projection; and said cap has a tubular shape that is closed at one end thereof and open at the other end, the open end cooperating in a hermetically sealing fashion with said annular seal.

4. A lambda module according to claim 1, wherein said cap is adapted to be pushed onto said module carrier frame and includes latching arms on both sides thereof and said receptacle portion includes preliminary latches and final latches, said latching arms, when the cap is being pushed onto said frame, first engage said preliminary latches and finally engage said final latches.

5. A lambda module according to claim 1, wherein said module housing has an opening connected to an internal space receiving said hybrid module, said opening being sealed by a pressure-equalizing membrane.

6. A lambda module according to claim 5, wherein said cap includes a protective tongue that covers said pressure-equalizing membrane when said cap is locked in position on said module carrier.

7. A lambda module according to claim 2, wherein said module carrier frame is adapted to allow insertion of the hybrid module from below into the space surrounded by said frame, and said frame having latching noses molded thereon for latching said hybrid module in position.

8. A lambda module according to claim 2, wherein said U-shaped module carrier frame is adapted to allow said hybrid module to be inserted sideways therein.

9. A lambda module according to claim 1, wherein the receptacle portion of the module housing has a sealing cushion inserted therein, said sealing cushion having a separate opening for receiving each contact of said mating plug to be plugged into said receptacle portion.

10. A lambda module according to claim 1 in combination with a mating plug, wherein said receptacle portion of the module housing and said mating plug both have mechanical encoding means preventing said mating plug from being inserted into said receptacle portion with incorrect orientation.

11. The combination according to claim 10, wherein said mating plug has pivotally mounted thereon a tightening clip including slotted links and said receptacle portion of the module housing has pins provided thereon, said pins cooperating with said slotted links so as to allow pulling a said mating plug into a latching position into said receptacle portion when said tightening clip as being pivoted.

12. The combination of claim 11, wherein said mating plug has latching elements adapted to engage latching elements provided on said tightening clip for latching said tightening clip in an open position thereof in which it is pivoted backward.

13. The combination of claim 11, wherein said receptacle portion of the module housing includes a flexible latching nose adapted to engage a rear edge of said tightening clip when said tightening clip is moved into its latching position.

14. The combination according to claim 10, wherein said mating plug has its interior divided into a plurality of tubular chambers, each chamber being adapted to receive one electrical contact.

* * * * *